United States Patent
Samain et al.

(10) Patent No.: US 6,342,235 B1
(45) Date of Patent: *Jan. 29, 2002

(54) SOLID COSMETIC COMPOSITION AND USES

(75) Inventors: Henri Samain, Bievies; Isabelle Cretois, Paris,, both of (FR)

(73) Assignee: L'Oreal, S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/860,669

(22) PCT Filed: Oct. 31, 1996

(86) PCT No.: PCT/FR96/01723

§ 371 Date: Aug. 26, 1997

§ 102(e) Date: Aug. 26, 1997

(87) PCT Pub. No.: WO97/17053

PCT Pub. Date: May 15, 1997

(30) Foreign Application Priority Data

Nov. 6, 1995 (FR) .............................. 95 13094

(51) Int. Cl.⁷ .............................. A61K 6/00; A61K 7/00; A61K 7/06; A61K 7/075
(52) U.S. Cl. .................... 424/401; 424/70.1; 424/70.9; 424/70.21; 424/70.22; 424/70.24; 424/70.27; 424/70.28; 424/74; 424/63
(58) Field of Search .......................... 424/70.11, 70.13, 424/401, 70.1, 70.9, 70.21, 70.22, 70.24, 70.27, 70.28, 74, 63, 10.11

(56) References Cited

U.S. PATENT DOCUMENTS

| | | | | |
|---|---|---|---|---|
| 3,959,463 A | * | 5/1976 | Nersesian et al. | 424/70.13 |
| 4,126,142 A | * | 11/1978 | Saute | 132/7 |
| 4,330,438 A | | 5/1982 | Dierassi et al. | |
| 4,847,076 A | * | 7/1989 | Deshpande et al. | 424/70.13 |
| 4,859,456 A | * | 8/1989 | Marschner | 424/70.13 |
| 5,246,694 A | * | 9/1993 | Birthwistle | 424/70.31 |
| 5,635,171 A | * | 6/1997 | Nadaud | 424/78.03 |
| 5,658,575 A | * | 8/1997 | Ribier et al. | 424/401 |
| 5,679,328 A | * | 10/1997 | Dupuis | 424/70.13 |

FOREIGN PATENT DOCUMENTS

| | | | |
|---|---|---|---|
| EP | 0170927 | * | 12/1986 |
| EP | 0 272 919 | | 6/1988 |
| EP | 0 615 744 A2 | | 9/1994 |
| EP | 0 615 744 A3 | | 9/1994 |
| FR | 2 670 673 | | 6/1992 |
| GB | 902808 | * | 8/1962 |
| WO | 95/11000 | | 4/1995 |

* cited by examiner

*Primary Examiner*—Thurman K. Page
*Assistant Examiner*—Humera N. Sheikh
(74) *Attorney, Agent, or Firm*—Finnegan, Henderson, Farabow, Garrett & Dunner, L.L.P.

(57) ABSTRACT

Solid, non-detergent and non-tacky cosmetic compositions having a water absorption capacity greater than 50 mg are disclosed. Said compositions are generally provided as sticks, pencils or bars and may be used to produce a variety of solid products for make-up, for skin, scalp, hair or mucosal care and/or treatment, and for styling and/or setting keratin fibres such as hair.

33 Claims, No Drawings

SOLID COSMETIC COMPOSITION AND USES

The present invention relates to solid nondetergent cosmetic compositions which are nonadhesive and which have a good water absorption capacity and to their use in cosmetics.

In the cosmetics industry various forms of products are known in the form of a solid, especially in the field of makeup, like sticks of lip rouge, of foundation or of eye shadow; in the field of skin or lip care such as lip repair pencils and depigmenting or hydrating sticks; in the field of hygiene, like deodorant sticks.

These compositions have some disadvantages. As the active substances are delivered directly from the solid composition, these various compositions must be presented in a hermetic packaging in order not to dry out in air or in order not to stain. Many solid compositions are formulated based on waxes; they have a greasy character which is not appreciated by the users.

Furthermore, some compositions such as hair-dressing products are generally presented in fluid form such as gels or mousses. It has appeared advantageous to be able to have product available in the form of a solid.

The Applicant has surprisingly discovered novel cosmetic compositions in the form of a solid exhibiting special characteristics.

The compositions according to the invention have the advantage of being hydratable at the surface in contact with water or a wet surface at the time of use, of permitting a good release of the cosmetically active products onto the keratinous material to be treated, of rapidly regaining, after drying, their initial solid form without deterioration and of being capable of being subsequently employed again merely by hydration at the surface.

The compositions according to the invention also have the advantage of being able to contain hydrophobic and/or lipophilic compounds, dispersed without the aid of surfactant.

The compositions according to the invention can be presented in the form of a stick, pencil or cake and in themselves constitute novel types of products for makeup, such as lipsticks, foundations and eye shadows; novel types of products for hair care and/or conditioning, such as hard hair-styling gels; novel types of products in stick form for face or body care.

The subject of the invention is therefore a nondetergent cosmetic composition in the form of a solid, characterized in that it is hydratable and that it does not have an adhesive feel in the nonhydrated state.

The term nondetergent means that the composition does not make it possible to remove from a solid medium such as, for example, the skin or the hair, the soiling which adheres thereto by dispersing or dissolving it.

Hydratable is intended according to the invention to mean a composition which has a water absorption capacity according to the test described below which is higher than 50 mg, preferably higher than 100 mg and lower than 3000 mg and more particularly between 200 and 1200 mg.

A composition which does not have an adhesive feel is intended according to the invention to mean a composition the adhesive bonding of which in the nonhydrated state defined according to the test described below is lower than 0.2 g, preferably between 0 and 0.1 g.

The nonhydrated state corresponds to the initial state of the composition, more particularly before use, that is to say before coming into contact with water or a wet surface.

The adhesive bonding of the composition in the nonhydrated state is determined by the weight of product pulled off by an absorbent paper applied for 10 seconds to the solid composition. The composition is in a round Petri dish of 4 cm diameter, the composition has a thickness of 8 mm over a diameter of 4 cm. The surface of the composition is planar and horizontal. A square piece of absorbent paper (Sopalin of weight per unit area equal to 45 g/m$^2$) of 4 cm$^2$ (2 cm×2 cm) which has been weighed beforehand ($W_1$) is applied. After 10 seconds' contact time the paper is pulled off and is weighed again ($W_2$) and the quantity of product pulled off is calculated ($W_2-W_1$).

The water absorption capacity is determine, by the weight of water absorbed in 10 seconds by the solid composition.

The composition is in a round Petri dish of 4 cm diameter, the composition has a thickness of 8 mm over a diameter of 4 cm. The surface of the composition is planar and horizontal. The dish containing the composition is weighed and then 5 g of water are poured onto the composition. After 10 seconds' contact time the unabsorbed water is removed. The dish is weighed again and the quantity of water absorbed is calculated.

The rigid compositions according to the invention generally exhibit a resistance to compression higher than or equal to 50 grams, at ambient temperature, after entry by a cylindrical probe of revolution which has a diameter of 0.8 cm into the gel matrix in a thickness of 5 mm, at a speed of 1 mm/s, holding said probe in the gel matrix for 15 seconds and withdrawing said probe from the gel matrix at a speed of 1 mm/s; the resistance to compression being measured with a texture analyzer of the TAXT2 type, marketed by the Rheo company.

The resistance to compression is preferably lower than 300 g.

Preferably, in the case of the rigid compositions in accordance with the invention, a curve is observed relating to the rigidity of the gel and to the deposition of the gel on the probe as a function of time, in conditions as defined above, which exhibits a positive peak corresponding to the force of compression of the gel after entry of the probe, but exhibiting no negative peak corresponding to a deposition of gel on the probe after withdrawal of the latter or exhibiting a negative peak smaller than 1 g, preferably smaller than 0.2 g.

More particularly, the composition includes at least one gelling agent in a cosmetically acceptable medium.

The cosmetically acceptable medium is preferably aqueous, that it is to say that it includes either only water or water and a solvent such as, for example, ethanol, propylene glycol, butylene glycol, isopropanol, glycol ethers such as the $C_1$–$C_4$ alkyl ethers of mono-, di- or tripropylene glycol, mono-, di- or triethylene glycol, dipropylene glycol, diethylene glycol and mixtures thereof.

Of course, the maximum quantity of water and/or of solvents is limited by the fact that the composition according to the invention must be in the form of a solid and must exhibit the characteristics described above.

According to the invention the gelling agents are preferably water-soluble or hydrophilic.

The gelling agents present in the compositions of the invention are preferably chosen from the group made up of:

extracts of algae, such as agar, carrageenans, alginates;

extracts of seeds, such as carob gum, guar gum and their derivatives;

exudates of plants, such as gum arabic, karaya gum, gum tragacanth and gatty gum;

exudates of microorganisms, such as xanthan gum, cellulose or its derivatives such as carboxymethyl cellulose, hydroxypropylcellulose, methylcellulose, hydroxypropylmethylcellulose or hydroxyethylcellulose and celluloses modified especially by grafting of an alkyl group;

extracts of fruits, such as pectins;

gelling agents of animal origin, such as gelatin and caseinates;

water-soluble gelling synthetic polymers such as crosslinked polyacrylic acids such as "Carbopol" or "Pemulen" from Goodrich;

silicon derivatives such as synthetic hectorites like the products "Laponite RD and RDS" sold by Waverly, aluminum and magnesium silicates like the product "Veegum" sold by Vanderbilt;

mixtures of the above compounds.

The gelling agents are preferably chosen from:

extracts of seeds, such as carob gum, guar gum and their derivatives;

extracts of algae, such as agar, carrageenans, alginates;

and mixtures thereof.

Still more particularly, nonionic or ionic guar gums and mixtures of carob gum and of carrageenans are employed according to the invention.

The guar gums are more particularly modified with $C_1$–$C_6$ hydroxyalkyl groups.

Among the hydroxyalkyl groups the hydroxymethyl, hydroxyethyl, hydroxypropyl and hydroxybutyl groups may be mentioned by way of example.

These guar gums are well known in the state of the art and can, for example, be prepared by reacting the corresponding alkene oxides such as, for example, propylene oxides with guar gum so as to obtain a guar gum modified with hydroxypropyl groups.

The degree of hydroxyalkylation, which corresponds to the number of alkylene oxide molecules consumed by the number of free hydroxyl functional groups present on the guar gum, preferably varies from 0.4 to 1.2.

Such nonionic guar gums optionally modified with hydroxyalkyl groups are, for example, sold under the 30 trade names Jaguar HP8, Jaguar HP60 and Jaguar HP120 by Meyhall, and the names Jaguar DC 293 and Jaguar HP 105 by Rhône Poulenc or under the name Galactasol 4H4FD2 by Agualon.

The ionic guar gums are more particularly cationic guar gums comprising, for example, trialkylammonium cationic groups. Preferably 2 to 30% and still more preferably 5 to 20% of the number of the hydroxyl functional groups in these guar gums carry trialkylammonium cationic groups.

Among these trialkylammonium groups the trimethylammonium and triethylammonium groups may be mentioned very particularly.

Still more preferably, these groups represent from 5 to 20% by weight relative to the total weight of the modified guar gum.

According to the invention a guar gum modified with 2,3-epoxypropyltrimethylammonium chloride is preferably employed.

These guar gums modified with cationic groups are products which are already known per se and are described, for example, in patents U.S. Pat. No. 3 589 578 and U.S. Pat. No. 4 0131 307. Such products are furthermore sold, especially under the trade names of Jaguar C 13 S, Jaguar C 15 and Jaguar C 17 by Meyhall.

The gelling agent is generally present in concentrations higher than 8% by weight relative to the total weight of the composition, preferably, in concentrations ranging from 8 to 90% by weight relative to the total weight of the composition and more particularly still between 8 and 70% by weight.

The compositions according to the invention may also contain one or several nonionic, anionic, cationic or amphoteric surfactants usually employed in cosmetics. The quantity of surfactant agent which is employed is preferably from 0.5 to 30% relative to the total weight of the composition. The nature and the concentration of these surfactants are chosen by a person skilled in the art so as not to impart a detergent character to the composition. The composition preferably contains less than 4% by weight of detergent surfactants.

The compositions according to the invention may also contain one or several anionic, cationic, nonionic, amphoteric or zwitterionic polymers. These polymers may be present in concentrations of between 0.1 and 70% by weight relative to the total weight of the composition and preferably between 0.5 and 30% by weight.

The polymers, especially the fixing polymers are preferably present in a polymer/gelling agent weight concentration ratio of between 0.5 and 2.

A fixing polymer is intended to mean any polymer the purpose of which is to temporarily fix the shape of the keratinous fibers such as, for example, the hair or eyelashes.

The polymers may be dissolved in the cosmetically acceptable medium or employed in the form of aqueous dispersions of insoluble particles (latices or pseudolatices).

The compositions according to the invention may contain additives which are usually employed in cosmetic compositions. It is possible in particular to mention antioxidants or anti-free radical agents; inorganic insoluble fillers and/or organic fillers, of lamellar or spherical structure, pigments or dyes, silicones, oils and/or waxes of animal, plant, inorganic or synthetic origin, hydrating or moisturizing agents such as glycerin and collagen; UV screening agents, perfumes, antidandruff agents, conditioning agents and deodorants.

These additives may be present in the final composition in a quantity of 0 to 80%, preferably of 0.5 to 50% by weight relative to the total weight of the composition and more particularly still between 0.5 and 15% by weight.

Of course, a person skilled in the art will take care to choose this or these optional additional compounds and/or their quantities in such a way that the advantageous properties intrinsically attached to the composition in accordance with the invention are not, or are not substantially, impaired by the addition(s) envisaged.

The compositions according to the invention can be prepared, for example, merely by mixing or by mixing followed by kneading and extrusion in an extruder. The extruder is preferably a twin-screw extruder.

The extruder which can be employed for the process is chosen from twin-screw extruders such as those described in the application FR 94-00756 filed on Jan. 25, 1994.

The raw materials are introduced, at the entry of the twin-screw extruder, into the feed zone at ambient temperature, preferably at approximately 20° C., and are then brought into the conveying zone at a temperature, preferably, at approximately 50° C., and are then kneaded and compressed in various zones of the extruder which are maintained at a temperature preferably ranging from 60 to 100° C.; the mass obtained is conveyed toward the exit of the extruder and extruded through a die.

During the kneading and compression stage the gelling agent in contact with the cosmetically acceptable medium forms, after extrusion, a gelled network constituting the matrix of the final products. The extruded mass leaves the die in the form of "sausages" of given diameter according to the die employed, which can sub-sequently be cut and formed into a stick, pencil with an aqueous lead or a solid cake. Other forms can, of course, be produced by choosing appropriate dies and devices for forming the final products which are suited to the form sought after.

The solid compositions according to the invention may be presented in various forms depending on the application chosen. The most widely employed forms are sticks, pencils or cakes.

The compositions according to the invention may be products for makeup, such as lipsticks, foundations, eye shadows, blushers, products for hiding rings under the eyes, and mascaras. The makeup compositions are stored in the nonhydrated state and, at the time of use, are hydrated at the surface by contact with water or a wet surface to deliver the active substances for the makeup and then, after drying, regain their initial form without deterioration, ready for another use in the same conditions.

Another subject of the invention is therefore a process for making up the lips, the face, the surround of the eyes, the cheeks, the eyelashes, the eyebrows or the eyelids, characterized in that a solid composition as defined above is employed, that the latter is wetted at the surface with water or a wet surface and that said hydrated composition is applied to the lips, the face, the surround of the eyes, the cheeks, the eyelashes, the eyebrows or the eyelids.

Another subject of the invention is also a process for making up the lips, the face, the surround of the eyes, the cheeks, the eyelashes, the eyebrows or the eyelids, characterized in that a solid composition as defined above is employed and that said nonhydrated composition is applied to a wet surface such as the lips, the face, the surround of the eyes, the cheeks, the eyelashes, the eyebrows or the eyelids.

The compositions according to the invention may also be products for the care and/or the conditioning and/or the hygiene of the skin, the mucosae, the scalp or the hair. They are applied to keratinous materials, at the time of use, merely by hydration at the surface in contact with water or a wet surface in order to deliver the compounds and then, after drying, regain their initial form without deterioration, ready for another use in the same conditions.

Among the care, conditioning or hygiene products which can be envisaged there may be mentioned, for example, in capillary applications: solid gels for styling in the form of cake or stick; in skin care: hydrating and slimming agents in the form of stick or cake, products for lip care in the form of stick or of pencil; in hygiene: products for shaving and deodorants in stick or cake form.

Another subject of the invention consists of a process of cosmetic treatment for the care and/or conditioning and/or the hygiene of the skin, the hair, the scalp or the mucosae, characterized in that a solid composition as defined above is employed, that the latter is wetted at the surface with water or a wet surface and that said partially hydrated composition is applied to the skin, the hair, the eyelashes, the eyebrows, the scalp or the mucosae.

Another subject of the invention consists of a process of cosmetic treatment for the care and/or conditioning and/or the hygiene of the skin, the hair, the scalp or the mucosae, characterized in that a solid composition as defined above is employed and that said nonhydrated composition is applied to a wet surface such as to the skin, the hair, the eyelashes, the eyebrows, the scalp or the mucosae.

According to a particular embodiment of the invention the compositions are products for styling and/or shaping keratinous fibers such as the hair or the eyelashes.

Another subject of the present invention is a process for styling and/or shaping keratinous fibers such as the hair, characterized in that a solid composition as defined above is employed, that the latter is wetted at the surface with water or a wet surface and that said hydrated composition is applied to said keratinous fibers.

Another subject of the present invention is a process for styling and/or shaping keratinous fibers such as the hair, characterized in that a solid composition as defined above is employed and that said nonhydrated composition is applied to a wet surface such as said keratinous fibers.

In what follows or what precedes, the percentages are expressed by weight, unless stated otherwise.

The examples which follow are used to illustrate the invention without, however, limiting its scope.

EXAMPLES

Example 1

Solid styling gel

A solid gel of the following composition was prepared:

| | |
|---|---|
| Hydroxypropylated guar gum (Jaguar HP 60 from Meyhall) | 10.0% |
| Ethanol | 17.2% |
| Stabilizer | q.s. |
| Water | 100.0% |

The guar gum is introduced by sprinkling with stirring into cold water and ethanol. After a few minutes the composition is cast in a mold and then after a wait of approximately 1 hour the composition is demolded in the form of a solid.

According to the test described above the adhesive bonding of the composition is approximately 60 mg.

According to the test described above the water absorption capacity of the composition is approximately 435 mg.

The product is hydrated by handling in wet hands and the hydrated and recovered product on the hands is then distributed onto the head of hair by running the hands through the wet hair. The hair is next shaped and then dried under a hood.

The composition has a good styling effect. The hair is gleaming and has a natural feel.

Example 2

(Comparative) Solid styling gel

A solid gel of following composition is prepared:

| | |
|---|---|
| Vinyl acetate/vinylpyrrolidone copolymer (Luviscol VA 64 from BASF) | 15.0 g |
| Acrylic copolymer (Synthalen K from 3 V) | 4.40 g |
| Ethanol | 17.2 g |
| Stabilizer | q.s. |
| Water | q.s. 100.0 g |

The polymers are introduced by sprinkling with stirring into cold water and ethanol containing the stabilizer. After a few minutes the composition is cast in a mold and then after a wait of approximately 1 hour the composition is demolded in the form of a solid.

According to the test described above the adhesive bonding of the composition is approximately 1330 mg.

It therefore has an adhesive feel; it cannot be handled in the nonhydrated state.

The composition has a styling effect but the hair is rough and has an adhesive feel.

Example 3

Solid styling gel

A solid gel of following composition is prepared:

| | |
|---|---|
| Hydroxypropylated guar gum (Jaguar HP 60 from Meyhall) | 15.0 g |
| Ethanol | 17.2 g |
| Stabilizer | q.s. |
| Water | q.s. 100.0 g |

The guar gum is introduced by sprinkling with stirring into cold water and ethanol containing the stabilizer. After a few minutes the composition is cast in a mold and then after a wait of approximately 1 hour the composition is demolded in the form of a solid.

According to the test described above the adhesive bonding of the composition is approximately 61 mg.

According to the test described above the water absorption capacity of the composition is approximately 386 mg.

When applied to the hair, this styling gel has the same properties as that of Example 1.

Example 4

Solid styling gel

A solid gel of following composition was prepared:

| | |
|---|---|
| Carob gum | 35.0 g |
| Carrageenan gum | 35.0 g |
| Stabilizer | q.s. |
| Water | q.s. 100.0 g |

The raw materials are introduced at the entry of a twin-screw extruder at a temperature of 30° C. They are then brought into the conveying zone at a temperature of 50° C. and are then kneaded and compressed in various zones of the extruder which are maintained at approximately 80–90° C. The mass thus kneaded and compressed is conveyed toward the exit of the extruder and extruded, for example, through a die 3 cm in diameter. The time of passage through the extruder is approximately 15 seconds. The speed of rotation of the screws is 500 revolutions/minute. The "sausages" obtained at the die exit are reduced into the form of small sticks 10 cm in length by means of a cutter at the exit of the extruder.

According to the test described above the adhesive bonding of the composition is approximately 0 mg.

According to the test described above the water absorption capacity of the composition is approximately 550 mg.

When applied to the hair, this styling gel has the same properties as that of Example 1.

What is claimed is:

1. A solid, nondetergent cosmetic composition having a water absorption capacity higher than 50 mg, an adhesive bonding in the nonhydrated state lower than 0.2 g, and a resistance to compression higher than or equal to 50 g, said composition including at least one gelling agent in a cosmetically acceptable medium, said gelling agent being present in a concentration ranging from 8% to 90% by weight relative to the total weight of the composition.

2. A composition according to claim 1, wherein said water absorption capacity ranges from 100 to 3000 mg.

3. A composition according to claim 2, wherein said water absorption capacity ranges from 200 to 1200 mg.

4. A composition according to claim 1, wherein said adhesive bonding ranges from 0 to 0.1 g.

5. A composition according to claim 1, wherein said at least one gelling agent is water-soluble or hydrophilic.

6. A composition according to claim 1, wherein said at least one gelling agent is water-soluble and is present in a concentration ranging from 8% to 70% by weight relative to the total weight of the composition.

7. A composition according to claim 1, wherein said at least one gelling agent is contained in an aqueous cosmetically acceptable medium.

8. A composition according to claim 1, wherein said at least one gelling agent is water-soluble and is selected from:
    extracts of algae;
    extracts of seeds;
    exudates of plants;
    exudates of microorganisms;
    extracts of fruits;
    gelling agents of animal origin;
    water-soluble gelling synthetic polymers; and
    silicon derivatives.

9. A composition according to claim 8, wherein said at least one gelling agent is selected from agar, carrageenans, aliginates, carob gum, guar gums and their derivatives, gum arabic, karaya gum, gum tragacanth, gatty gum; xanthan gum, celluloses and their derivatives; pectins; gelatin, caseinates; crosslinked polyacrylic acids; synthetic hectorites and aluminum and magnesium silicates.

10. A composition according to claim 9, wherein said at least one gelling agent is selected from guar gums and their derivatives and from mixtures of carrageenan gums and carob gum.

11. A composition according to claim 1, wherein said composition also includes at least one adjuvant selected from pigments, surfactants, antioxidants, anti-free radical agents, hydrating agents, silicones, moisturizers, UV screening agents, oils and waxes of animal, plant, mineral and synthetic origin and anionic, cationic, nonionic, amphoteric and zwitterionic polymers.

12. A composition according to claim 1, wherein said composition further includes at least one polymer and at least one gelling agent in a polymer/gelling agent weight concentration ratio ranging from 0.5:1 to 2:1.

13. A composition according to claim 1, wherein said composition is in the form of a stick, pencil or cake.

14. A composition according to claim 1, wherein said composition is a makeup product.

15. A composition according to claim 1, wherein said composition is a product for the care and/or the conditioning and/or the hygiene of the skin, the mucosae, the scalp or the hair.

16. A composition according to claim 1, wherein said composition is a product for the styling and/or the shaping of keratinous fibers.

17. A process for the care and/or the conditioning and/or the hygiene of the skin, the hair, the scalp, the eyelashes or the mucosae, comprising the steps of hydrating the composition according to claim 1, and applying said hydrated composition to the surface of the skin, the hair, the eyelashes, the scalp or the mucosae.

18. A process for making up the lips, the face, the eyelashes, the eyebrows or the eyelids, comprising the steps of hydrating the composition according to claim 1, and applying said hydrated composition to the lips, the face, the eyelashes, the eyebrows or the eyelids.

19. A process according to claim 18, wherein said composition is hydrated by applying said composition to wet lips, wet face, wet eyelashes, wet eyebrows or wet eyelids.

20. A process for styling and/or shaping keratinous fibers, comprising the steps of hydrating a composition according to claim 1 and applying said hydrated composition to the surface of said keratinous fibers.

21. A process for styling and/or shaping keratinous fibers according to claim 20, wherein said composition is hydrated by being applied to a wet surface of keratinous fibers.

22. A composition according to claim 16, wherein said keratinous fibers are hair or eyelashes.

23. A process according to claim 17, wherein said step of hydrating occurs during the step of applying to said surface.

24. A process according to claim 23, wherein said step of hydrating occurs during the step of applying said composition to the surface of wet skin, wet hair, wet eyelashes, wet scalp or wet mucosae.

25. A process according to claim 17 wherein said composition is hydrated by contact with water before said step of applying said composition to said surface.

26. A process according to claim 17 wherein said composition is hydrated by contact with water at the surface of dry skin, dry hair, dry eyelashes, dry scalp or dry mucosae after said applying step.

27. A process according to claim 18 wherein said composition is hydrated by contact with water and then said composition is applied to said surface.

28. A process according to claim 18, wherein said step of hydrating occurs during the step of applying said composition to the surface of wet lips, wet face, wet eyelashes, wet eyebrows or wet eyelids.

29. A process according to claim 18, wherein said composition is hydrated by contact with water at the surface of dry lips, dry face, dry eyelashes, dry eyebrows or dry eyelids after said applying step.

30. A process according to claim 20 wherein said composition is hydrated by contact with water before said step of applying said composition to said surface of said keratinous fibers.

31. A process according to claim 20 wherein said composition is hydrated by contact with water at the surface of dry keratinous fibers.

32. A process according to claim 20, wherein said keratinous fibers are hair.

33. A process according to claim 21, wherein said keratinous fibers are hair.

* * * * *

UNITED STATES PATENT AND TRADEMARK OFFICE
CERTIFICATE OF CORRECTION

PATENT NO.   : 6,342,235 B1
DATED        : January 29, 2002
INVENTOR(S)  : Samain et al.

It is certified that error appears in the above-identified patent and that said Letters Patent is hereby corrected as shown below:

Title page,
Item [75], Inventors: "Paris,," should read -- Paris, --.

Column 8,
Line 24, "aliginates," should read -- aliginates; --.

Signed and Sealed this

Thirtieth Day of April, 2002

Attest:

JAMES E. ROGAN
*Attesting Officer*   *Director of the United States Patent and Trademark Office*